United States Patent [19]

Wu

[11] Patent Number: 5,315,028

[45] Date of Patent: May 24, 1994

[54] OLEFINIC PROCESS FOR PREPARING ARYL-SUBSTITUTED ALIPHATIC CARBOXYLIC ESTERS

[75] Inventor: Tse-Chong Wu, Baton Rouge, La.

[73] Assignee: Ethyl Corporation, Richmond, Va.

[21] Appl. No.: 62,527

[22] Filed: May 12, 1993

[51] Int. Cl.$^5$ .................... C07C 69/76; C07C 51/10
[52] U.S. Cl. .................................. 560/105; 562/406; 560/9; 560/20; 560/21; 560/55; 560/56; 560/100
[58] Field of Search ............... 562/400; 560/105, 9, 560/20, 21, 55, 56, 100

[56] References Cited

U.S. PATENT DOCUMENTS 5,166,419 11/1992 Towamoto et al. ............. 560/105

*Primary Examiner*—Paul J. Killos
*Attorney, Agent, or Firm*—Richard J. Hammond

[57] ABSTRACT

A new process for preparing aryl substituted aliphatic carboxylic acid esters is provided. A 1-aryl substituted olefinic compound is reacted with carbon monoxide in the presence of an alcohol in anhydrous conditions at a temperature between about 25° C. and about 200° C. An excess of several moles of anhydrous alcohol is preferred. An acid such as hydrochloric acid may also be added. As catalyst, a mixture of a palladium compound and a copper compound with at least one acid-stable ligand are present.

43 Claims, No Drawings

_5,315,028_

OLEFINIC PROCESS FOR PREPARING ARYL-SUBSTITUTED ALIPHATIC CARBOXYLIC ESTERS

TECHNICAL FIELD

This invention relates to a process for preparing aryl-substituted aliphatic carboxylic acid esters.

BACKGROUND OF THE INVENTION

Among the processes known for preparing 2-(4-isobutylphenyl)propionic acid or esters thereof is that of Shimizu et al. (U.S. Pat. No. 4,694,100, issued September, 1987), who teach the reaction of p-isobutylstyrene with carbon monoxide and water or alcohol in the presence of a palladium catalyst and a mineral acid, e.g., HCl. This patent also teaches the alternative reaction of p-isobutylstyrene with carbon monoxide and hydrogen in the presence of a metal complex carbonyl catalyst to produce 2-(4-isobutylphenyl)propionaldehyde, which is then oxidized to produce the desired product. The preparation of the starting material for this reaction is disclosed as the reaction of isobutylbenzene with acetaldehyde in the presence of sulfuric acid, producing 1,1-bis(4-isobutylphenyl)ethane, which is then catalytically cracked to produce p-isobutylstyrene and isobutylbenzene.

Another process for preparing ibuprofen is that of European Patent Application 284,310 (Hoechst Celanese, published September, 1988), which teaches that ibuprofen can be prepared by carboxylating 1-(4-isobutylphenyl)ethanol with carbon monoxide in an acidic aqueous medium and in the presence of a palladium compound/phosphine complex and dissociated hydrogen and halide ions, which are preferably derived from a hydrogen halide. This process has the disadvantage of starting with 1-(4-isobutylphenyl)ethanol, a compound which is not economical to make by known processes.

Gardano et al. (U.S. Pat. No. 4,536,595, issued August, 1985) teach the preparation of alkaline salts of certain alpha-arylpropionic acids by reaction with carbon monoxide, at substantially ambient temperature and pressure conditions, of the corresponding arylethyl secondary halide in an anhydrous alcoholic solvent in the presence of alkaline hydroxides and, as catalyst, a salt of cobalt hydrocarbonyl.

Alper et al. in _J. Chem. Soc. Chem. Comm._, 1983, 1270–1271, discloses that alkenes can react with carbon monoxide, water, hydrochloric acid and a mixture of palladium and copper to produce the hydrocarboxylated product, branched chain carboxylic acid. Oxygen is necessary to succeed in the reaction. Subsequently, Alper et al. have disclosed similar catalyst systems, but employing a chiral ligand, as being successful in asymmetric hydrocarboxylation reactions. See Alper et al., PCT Application, WO 91 03,452 and _J. Am. Chem. Soc._, 112, 2803–2804 (1990).

Another process for preparing ibuprofen is that of Japanese Patent Application (Kokai) No. 59-10,545 (Mitsubishi Petrochemical, published January, 1984), which teaches that ibuprofen can be prepared by reacting p-isobutylstyrene with carbon monoxide and water or alcohol in the presence of a palladium (II) catalyst and a peroxide, e.g., cumyl hydroperoxide.

THE INVENTION

In the following specification, the meaning of the substituent groups is as follows: "alkyl" means straight or branched chain alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutYl, nonyl, decyl, dodecyl, tetradecyl, hexadecyl, octadecyl and eicosyl, and the like (for the purposes of this definition, "alkyl" is also "aliphatic");

"cycloalkyl" means cyclic alkyl having 3 to 7 carbon atoms and includes cyclopropyl, cyclobutyl, cyclopentyl, cyclohexyl, cycloheptyl and the like;

"substituted aryl" means phenyl or naphthyl substituted by at least one substituent selected from the group consisting of halogen (chlorine, bromine, fluorine or iodine), amino, nitro, hydroxy, alkyl, alkoxy which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptyloxy, octyloxy, nonyloxy and decyloxy, aryloxy including phenoxy and phenoxy substituted with halo, alkyl, alkoxy and the like, haloalkyl which means straight or branched chain alkyl having 1 to 8 carbon atoms which is substituted by a least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-diibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl, 2,2,3,3-tetrafluoropropyl and the like;

"alkyl-substituted cycloalkyl" means that the cycloalkyl moiety is cyclic alkyl having 3 to 7 carbon atoms and the alkyl moiety is straight or branched chain alkyl having 1 to 8 carbon atoms, and includes, for example, cyclopropylmethyl, cyclobutylmethyl, cyclopentylmethyl, cyclohexylmethyl, cycloheptylmethyl, 2-cyclopropylethyl, 2-cyclopentylethyl, 2-cyclohexylethyl, 3-cyclopropylpropyl, 3-cyclopentylpropyl, 3-cyclohexylpropyl, 4-cyclopropylbutyl, 4-cyclopentylbutyl, 4-cyclohexylbutyl, 6-cyclopropylhexyl, 6-cyclohexylhexyl and the like;

"alkylthio" means a divalent sulfur with alkyl occupying one of the valencies and includes the groups methylthio, ethylthio, propylthio, butylthio, pentylthio, hexylthio, octylthio and the like;

"heteroaryl" means 5 to 10 membered mono- or fused-heteroaromatic ring which has at least one heteroatom and includes those selected from the group consisting of nitrogen, oxygen and sulfur, and includes, for example, 2-furyl, 3-furyl, 2-thienyl, 3-thienyl, 2-pyridyl, 3-pyridyl, 4-pyridyl, pyrazolyl, imidazolyl, pyrimidinyl, pyridazinyl, pyrazinyl, benzimidazolyl, quinolyl, oxazolyl, thiazolyl, indolyl and the like;

"substituted heteroaryl" means 5 to 10 membered mono-or fused-heteroaromatic ring which has at least one heteroatom selected from the group consisting of nitrogen, oxygen and sulfur and which is substituted by at least one substituent selected from the group consisting of halogen, amino, nitro, hydroxy, alkyl, alkoxy and haloalkyl on the above-mentioned heteroaromatic nucleus;

"alkanoyl" means alkanoyl having 2 to 18 carbon atoms and includes, for example, acetyl, propionyl, butyryl, isobutyryl, pivaloyl, valeryl, hexanoyl, octanoyl, lauroyl, stearoyl and the like;

"aroyl" means benzoyl or naphthoyl;

"substituted aroyl[ means benzoyl or naphthoyl substituted by at least one substituent such including those selected from the group consisting of halogen, amino, nitro, hydroxy, alkyl, alkoxy and haloalkyl on the benzene or naphthalene ring;

"heteroarylcarbonyl" means that the heteroaryl moiety is 5 to 10 membered mono- or fused-heteroaromatic ring having at least one heteroatom selected from the group consisting of nitrogen, oxygen and sulfur as mentioned above, and includes, for example, furoyl, thinoyl, nicotinoyl, isonicotinoyl, pyrazolylcarbonyl, imidazolylcarbonyl, pyrimidinylcarbonyl, benzimidazolylcarbonyl and the like;

"substituted heteroarylcarbonyl" means the above-mentioned heteroarylcarbonyl which is substituted by at least one substituent selected from the group consisting of halogen, amino, nitro, hydroxy, alkoxy and haloalkyl on the heteroaryl nucleus; and includes, for example, 2-oxo-1,3-dioxolan-4-ylmethyl, 2-oxo-1,3-dioxan-5-yl and the like.

The present invention embraces any salts, racemates and individual optical isomers thereof of the compounds of the following formula (I) having a chiral carbon atom.

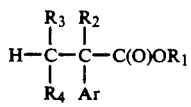   I where Ar, $R_1$, $R_2$, $R_3$ and $R_4$ are subsequently defined.

In accordance with the present invention, aryl-substituted aliphatic carboxylic acid esters are prepared by carboxylating an aryl-substituted, olefinic compound with carbon monoxide in a neutral or acidic anhydrous medium containing at least 1 mol of a $C_1$ to about $C_8$ linear or branched aliphatic alcohol per mol of olefinic compound at a temperature of between about 25° C. and about 200° C. and a carbon monoxide pressure of at least about one atmosphere in the presence of a mixture of (i) palladium metal or a palladium compound in which the palladium has a valence of 1 or 2 and (ii) a copper compound having a valence of 1 or 2 and at least one acid-stable ligand. In place of the aliphatic alcohol, an alcohol equivalent can be used. These include the trialkyl orthoalkonates, dialkyl ketals, alkyl formates, trialkyl borates, or titanium alkoxides. These materials provide a "source of alkoxide ions" as further defined herein. The esters may be readily converted to the corresponding free carboxylic acids or salts by well known conventional methods.

The olefinic-containing compound which is catalytically carboxylated in the practice of this invention has the formula:

   II where, Ar is unsubstituted or substituted aryl and $R_2$, $R_3$ and $R_4$ are hydrogen, alkyl, cycloalkyl, substituted or unsubstituted aryl, alkoxy, alkylthio, substituted or unsubstituted heteroaryl, alkanoyl, substituted or unsubstituted aroyl, substituted or unsubstituted heteroarylcarbonyl, trifluoromethyl or halo.

Preferably, in the compounds of formula II, Ar is unsubstituted or substituted aryl, $R_2$, $R_3$ and $R_4$ are hydrogen, $C_1$ to $C_2$ alkyl, substituted or unsubstituted phenyl or trifluoromethyl.

Most preferably Ar is phenyl substituted with alkyl or naphthyl substituted with alkoxy, $R_2$, $R_3$ and $R_4$ and are hydrogen, methyl or trifluoromethyl.

The catalytic carboxylation of the compound of formula II is conducted in an anhydrous medium (in the absence of water), at a temperature between about 25° C. and about 200° C., preferably about 25°–120C., and most preferably about 50°–100C. Higher temperatures can also be used. It has been found that a small advantage in yield is obtained by gradually increasing the temperature within the preferred ranges during the course of the reaction.

The partial pressure of carbon monoxide in the reaction vessel is at least about 1 atmosphere (14.7 psig) at ambient temperature (or the temperature at which the vessel is charged). Any higher pressures of carbon monoxide can be used up to the pressure limits of the reaction apparatus. A pressure up to about 3000 psig is convenient in the process. More preferred is a pressure from about 300 to about 3000 psig at the reaction temperature, and most preferred is a pressure from about 400 to about 800 psig. It should be noted that the presence of oxygen is undesirable in the hydrocarboxylation reaction of this invention. Hence, an atmosphere of 100% carbon monoxide is most preferred to carry out this process. Various inert gases can, however, be incorporated in the reaction mass (nitrogen, argon, etc.) the only criteria being that the process should not be slowed to the point of requiring exceptionally long periods to complete the reaction.

The carboxylation is conducted in the presence of at least about one mol of an anhydrous aliphatic alcohol per mol of the compound of formula II; however, an excess is preferred in order to assist in driving the reaction to completion. Although there is no real upper limit to the amount of alcohol except that imposed by practicality (e.g. the size of the reaction vessel), an amount up to about 100 mols per mol of the compounds of formula II is useful in the process. Further, controlling the amount of alcohol used in the process of this invention is advantageous in terms of producing the highest yields. Therefore, an amount from about 2 to about 50 mols of alcohol per mol of the compounds of formula II is preferred, and an amount from about 3 to about 24 mols of alcohol per mol of the such olefinic compound is most preferred. The product of the reaction is a carboxylic acid ester (where $R_1$ is alkyl). These compounds have the following formula:

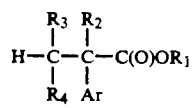   I where $R_1$ is hydrogen or alkyl and At, $R_2$, $R_3$ and $R_4$ are as previously defined.

Any alcohol which produces an ester of the carboxylic acid may be used in the practice of this invention. In a preferred embodiment, the lower aliphatic alcohols, are used. Examples of the alcohols to be used in this embodiment include methyl alcohol, ethyl alcohol, n-propyl alcohol, isopropyl alcohol, n-, iso- sec-, and tert-butyl alcohols, the pentyl alcohols, the hexyl alcohols, etc. Methyl alcohol is highly preferred, and ethyl alcohol is most highly preferred. Other alcohols, glycols, or aromatic hydroxy compounds may also be used. In the broadest sense, these alcohols provide a source of alkoxide ions for this reaction. However, any other "source of alkoxide ions" may also be used. The source of such alkoxide ions is from a compound selected from the group consisting of $HC(OR_1)_3$, $(R)_2C(OR_{11})_2$, $HC(O)OR_1$, $B(OR_1)_3$, $Ti(OR)_4$ and $Al(OR_1)_3$ where R is hydrogen or individually the same or different then $R_1$ and $R_2$ is as previously defined.

In a preferred embodiment of th is invention, the carboxylation reaction is initiated under neutral conditions, i.e., with no added acid. It can also be performed in the presence of an added acid. When acids are added, such acids include sulfuric acid, phosphoric acid or sulfonic acids. A hydrogen halide acid such as hydrochloric or hydrobromic acid is preferred. The hydrogen halide may be added as a gas phase or as a liquid phase (e.g., in the form of an alcoholic solution). Any concentration may be used. Hydrochloric acid is particularly preferred, at a concentration up to about 10%; more highly preferred is a concentration from about 10% to about 30%. The amount of acid added is such as to provide up to about 40 mols of hydrogen ion per mol of compound of formula II; more preferred is an amount to provide up to about 10 mols of hydrogen ion per mol of compound; the most preferred amount provides up to about 4 mols of hydrogen ion per mol of the compounds of formula II.

The catalytic carboxylation process of this invention is conducted in the presence of a reaction-promoting quantity of i) a mixture of palladium metal or a palladium compound in which the palladium has a valence of 1 or 2 and ii) a copper compound, with at least one acid-stable ligand. The compounds of palladium and copper are sometimes referred to as palladium and copper salts. Ligands which may be used include monodentate or multidentate electron-donating substances such as those containing elements P, N, 0 and the like, and those containing multiple bonds such as olefinic compounds. Examples of such acid-stable ligands are trihydrocarbylphosphines, including trialkyl- and triarylphosphines, such as tri-n-butyl-, tricyclohexyl-, and triphenylphosphine; lower alkyl and aryl nitriles, such as benzonitrile and n-propionitrile; ligands containing pi-electrons, such as an allyl compound or 1,5-cyclooctadiene; piperidine, piperazine, trichlorostannate(II), and acetylacetonate; and the like.

In one embodiment, palladium and copper compounds are inorganic salts and are added as a preformed complex of, for example, palladium (II) chloride or bromide, copper (II) chloride or bromide and carbon monoxide or any other similar complex. In a preferred embodiment, active catalytic species are formed in situ by the addition to the reaction mixture of the individual components, i.e., a ligand, a copper compound, and a palladium compound such as the inorganic salts of palladium (II) and copper(II). These inorganic salts include the chlorides, bromides, nitrates, sulfates, or acetates. In the most preferred embodiment, triphenylphosphine, copper(II) chloride, and palladium (II) chloride are used and are added individually or together, either simultaneously or sequentially.

The palladium metal or the palladium and copper compounds can be supported on carbon, silica, alumina, zeolite, clay and other polymeric materials and used as the heterogeneous catalysts.

The amount of copper and palladium metal or palladium compounds preferably employed is such as to provide from about 4 to about 8000 mols of the compound of formula II per mol of the mixture of metal and salt or of metal salts; more preferred is an amount to provide from about 10 to about 4000 mols of compound of formula II per mol of the mixture; the most preferred amounts provide from about 20 to 2000 mols of the compounds of formula II per mol of the metal salt mixture. The process of this invention is conducted in the presence of at least one mol of ligand per mol of the mixture of the metal and salt or metal salts. More preferably, about 2 to about 40 mols of ligand per mol of the mixture are present, and most preferably about 2 to about 20 mols of ligand per mol of the mixture are used.

The presence of a solvent is not required in the process of this invention, although it may be desirable in some circumstances. Those solvents which can be used include one or more of the following: ketones, for example, acetone, methyl ethyl ketone, diethyl ketone, methyl-n-propyl ketone, acetophenone, and the like; linear, poly and cyclic ethers, for example, diethyl ether, di-n-propyl ether, di-n-butyl ether, ethyl-n-propyl ether, glyme (the dimethyl ether of ethylene glycol), diglyme (the dimethyl ether of diethylene glycol), tetrahydrofuran, dioxane, 1,3-dioxolane, and similar compounds; and aromatic hydrocarbons, for example, toluene, ethyl benzene, xylenes, and similar compounds. Alcohols are also suitable as solvents, for example, methanol, ethanol, 1-propanol, 2-propanol, isomers of butanol, isomers of pentanol, etc. Acids and esters may also be used, such as formic or acetic acid or ethyl acetate, etc. When an ester or an alcohol is used as solvent, the product is the corresponding ester of the carboxylic acid. Most highly preferred are ethers, especially tetrahydrofuran. When solvents are used, the amount can be up to about 100 mL per gram of the compounds of formula II, but the process is most advantageously conducted in the presence of about 1 to 30 mL per gram of the compound of formula II.

In those specific embodiments of this invention in which an ester of ibuprofen is produced, the ester may be conveniently converted to the acid (ibuprofen itself) by conventional methods of hydrolysis.

The following examples are given to illustrate the process of this invention and are not intended as a limitation thereof.

EXAMPLE 1

A) Carbon monoxide (15 mL/min) was bubbled through THF (15 mL) for 10 min. $PdCl_2$ (0,029 g, 0.16 mmol) and $CuCl_2$ (0.050 g, 0.37 mmol) were added. The mixture was stirred at room temperature for 3-5 h. During this period, $PdCl_2$ and $CuCl_2$ were gradually dissolved and a yellow solid was gradually formed. This compound can be directly used as catalyst or it can be isolated by filtering and drying under CO atmosphere. Reference: D. Zargarian and H. Alper *Organometallics* 1991, 10, 2914.

B) The [$PdCl_2$/$CuCl_2$/CO] complex was freshly prepared as described above. To this catalyst (0.16 mmol) was added a solution of triphenylphosphine (0.13 g, 0.50 mmol), 4-isobutylstyrene (1.28 g, 8.0 mmol), MeOH (1 mL) and THF (15 mL). The mixture was transferred to a 100-mL Hastelloy B autoclave via syringe and the autoclave was then purged with CO (3×500 psig). The reactor was pressurized with CO (500 psig) and was agitated at 50° C. overnight (18 h). GC analysis of an aliquote found that the reaction mixture contained a 96:4 mixture of methyl 2-(4-isobutylphenyl)propionate and methyl 3-(4-isobutylphenyl)propionate in 97% conversion.

EXAMPLE 2

Example 2 was carried out in the same manner as Example 1 (See Table I).

EXAMPLE 3

$PdCl_2$ (0.029 g, 0.16 mmol) and $CuCl_2$ (0.050 g, 0.37 mmol) were charged into an autoclave (Hastelloy B, 100 mL) under nitrogen. A solution of triphenylphosphine (0.13 g, 0.50 mmol), 4-isobutylstyrene (1.28 g, 8.0 mmol), MeOH (1 mL), and methyl ethyl ketone (30 mL) was added via syringe. The autoclave was purged with CO (3×500 psig) and then filled with CO (500 psig). The mixture was agitated at 50° C. overnight (22 h). GC analysis of an aliquote found that the reaction mixture contained a 98:2 mixture of methyl 2-(4-isobutylphenyl)propionate and methyl 3-(4-isobutylphenyl)propionate in 98% conversion.

EXAMPLES 4 and 5

Examples 4 and 5 were carried out in the same manner as Example 3 (See Table I).

EXAMPLE 6

Pd on carbon (5 %, 0.17 g, 0.08 mmol), $CuCl_2$ (0.040 g, 0.30 mmol), and triphenylphosphine (0.13 g, 0.50 mmol) were charged into an autoclave (Hastelloy B, 100 mL) under nitrogen. A solution of 4-isobutylstyrene (1.28 g, 8.0 mmol), MeOH (1 mL), and methyl ethyl ketone (30 mL) was added via syringe. The autoclave was purged with CO (3×500 psig) and then filled with CO (700 psig). The mixture was agitated at 80°–85° C. for 44 h. GC analysis of an aliquote found that the reaction mixture contained a 95:5 mixture of methyl 2-(4-isobutylphenyl)propionate and methyl 3-(4-isobutylphenyl)propionate in 98% yield.

TABLE II-continued

A Comparison of the Rates of the Catalytic Hydrocarbomethoxylation

| Catalyst | Phosphine | % Conversion of Substrate to Product | | | |
|---|---|---|---|---|---|
| | | 2 h | 4 h | 6 h | 8 h |
| $PdCl_2$/10% HCl | $Ph_3P$ | 0 | 0 | 0 | 0 |
| $PdCl_2$ | $Ph_3P$ | 0 | 2 | 6 | 11 |

Conditions:
$P_{CO}$ = 500 psig
Temperature = 50° C.
Ligand = 3 equiv
Solvent = MEK/MeOH (30:1)
Substrate/catalyst = 50

It is obvious that many variations may be made in the products and processes set forth above without departing from the spirit and scope of this invention.

I claim:

1. A process for preparing an aryl-substituted aliphatic ester having the formula:

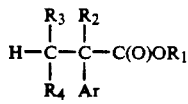

where $R_1$ is alkyl, $R_2$, $R_3$ and $R_4$ are hydrogen, alkyl, cycloalkyl, alkyl-substituted cycloalkyl, aryl either substituted or unsubstituted, alkoxy, alkylthio, heteroaryl either substituted or unsubstituted, alkanoyl, aroyl either substituted or unsubstituted, heteroarylcarbonyl either substituted or unsubstituted, trifluoromethyl or halo and Ar is unsubstituted or substituted aryl which comprises treating a compound of the formula:

where Ar, $R_2$, $R_3$ and $R_4$ are as previously defined and a compound of the formula $R_1OH$ where $R_1$ is as previously defined with carbon monoxide at a pressure of at least about 1 atmosphere and a temperature from about 25° C. to about 200° C. in the absence of oxygen and water and in the presence of an effective amount of a catalyst that is i) a mixture of palladium (O) or the salts of palladium and the salts of copper and (ii) at least one acid stable ligand.

2. A process of claim 1 wherein the palladium salt is a palladium (II) salt.

3. A process of claim 2 wherein the palladium salt is palladium (II) chloride.

TABLE I

Hydroesterification of isobutylstyrene

| # | Catalyst | Additives | Ligand | Solvent | P, psig | T, °C. | t, h | Yield | B/L |
|---|---|---|---|---|---|---|---|---|---|
| 1 | $PdCl_2/CuCl_2$, preformed | MeOH | $Ph_3P$, 3 eq | THF | 500 | 50 | 18 | 97 | 96/4 |
| 2 | $PdCl_2/CuCl_2$, preformed | MeOH | $Ph_3P$, 3 eq | MEK | 500 | 50 | 22 | 98 | 98/2 |
| 3 | $PdCl_2/CuCl_2$, in situ | MeOH | $Ph_3P$, 3 eq | MEK | 500 | 50 | 22 | 98 | 98/2 |
| 4 | $PdCl_2/CuCl_2$ | MeOH/ 10% HCl | $Ph_3P$, 3 eq | MEK | 500 | 80 | 14 | 93 | 96/4 |
| 5 | $PdCl_2/CuCl_2$ | HC(OEt)$_3$ | $Ph_3P$, 3 eq | MEK | 700 | 80 | 42 | 95 | 97/3 |
| 6 | 5% Pd/C, $CuCl_2$ | MeOH | $Ph_3P$, 6 eq | MEK | 700 | 80 | 44 | 98 | 95/5 |

TABLE II

A Comparison of the Rates of the Catalytic Hydrocarbomethoxylation

| Catalyst | Phosphine | % Conversion of Substrate to Product | | | |
|---|---|---|---|---|---|
| | | 2 h | 4 h | 6 h | 8 h |
| $PdCl_2/CuCl_2$, Preformed | $Ph_3P$ | 15 | 35 | 55 | 76 |
| $PdCl_2/CuCl_2$, In situ | $Ph_3P$ | 2 | 23 | 50 | 73 |
| $PdCl_2/CuCl_2$/10% HCl | $Ph_3P$ | 0 | 3 | 12 | 25 |

4. A process of claim 2 wherein the palladium salt is palladium (II) bromide.

5. A process of claim 1 wherein the ligand is a monodentate phosphine ligand.

6. A process of claim 1 wherein the ligand is a tri(hydrocarbyl)phosphine.

7. A process of claim 6 wherein the ligand is triphenylphosphine.

8. A process of claim 1 wherein the palladium salt is bis(triphenylphosphine)palladium (II) chloride or bromide and the copper salt is copper(I) chloride or copper(II) chloride.

9. A process of claim 1 wherein the amount of palladium metal or palladium salt and copper salt employed is such as to provide about 4–8000 mols of said olefinic compound per mol of palladium metal or palladium salt and copper salt.

10. A process of claim 9 wherein the palladium or palladium salt and copper salt and ligand are employed in amounts such as to provide about 2–20 mols of ligand per mol of palladium or palladium salt and copper salt in the reaction mixture.

11. A process of claim 10 wherein the palladium or palladium salt and copper salt and ligand are employed in amounts such as to provide about 2–12 mols of ligand per mol of palladium or palladium salt and copper salt in the reaction mixture.

12. A process of claim 1 wherein the carbonylation is conducted in the presence of from about 3 to about 24 mols of anhydrous methanol or anhydrous ethanol per mol of said olefinic compound.

13. A process of claim 1 wherein the carbonylation is conducted in the presence of added hydrogen halide.

14. A process of claim 13 wherein the hydrogen halide is hydrogen chloride.

15. A process of claim 13 wherein the hydrogen halide is hydrogen bromide.

16. A process of claim 13 wherein the hydrogen halide is added as a gas.

17. A process of claim 16 wherein the hydrogen halide is hydrogen chloride and the concentration in the anhydrous solution is a concentration up to about 30% (by weight) hydrogen chloride.

18. A process of claim 16 wherein the hydrogen halide is hydrogen chloride and the concentration in the anhydrous solution is a concentration up to about 10% (by weight) hydrogen chloride.

19. A process of claim 16 wherein the amount of hydrogen halide added is an amount up to about 40 mols per mol of said compound.

20. A process of claim 1 wherein the carbonylation is conducted in a solvent.

21. A process of claim 20 wherein the solvent is a ether.

22. A process of claim 21 wherein the solvent is tetrahydrofuran.

23. A process of claim 20 wherein the solvent is methyl ethyl ketone.

24. A process of claim 1 wherein the temperature is in the range of about 25°–120° C.

25. A process of claim 1 wherein the temperature is in the range of about 50°–100° C.

26. A process of claim 24 wherein the temperature is gradually increased during the reaction.

27. A process of claim 1 wherein the carbon monoxide pressure is in the range of about 300–3000 psig.

28. A process of claim 1 wherein the carbon monoxide pressure is in the range of about 400–800 psig.

29. A process for preparing ibuprofen which comprises carboxylating 4-isobutylstyrene with carbon monoxide in the absence of oxygen and in an anhydrous acidic medium containing tetrahydrofuran as a solvent and about 3–24 mols of anhydrous methanol or ethanol per mol of said 4-isobutylstyrene at a temperature in the range of about 25°–120° C. and a carbon monoxide pressure in the range of about 400–800 psig in the presence of a catalytically effective amount of (a) a mixture of a palladium (II) compound and a copper (II) compound and (b) at least one acid-stable monodentate phosphine ligand and in the presence of an amount of hydrogen chloride such as to provide an amount up to about 10 mols of hydrogen chloride per mol of 4-isobutylstyrene.

30. A process of claim 29 wherein the palladium (II) compound is palladium (II) chloride the copper (II) compound is copper(II) chloride and the ligand is triphenylphosphine.

31. A process of claim 29 wherein the palladium, the copper, and the ligand are present in amounts such as to provide about 200–2000 mols of said 4-isobutylstyrene per mol of the mixture of palladium and copper compounds and about 2–20 mols of ligand per mol of the mixture of palladium and copper compounds.

32. A process of claim 29 wherein the hydrogen chloride is added as an anhydrous solution with a concentration from about 10% (by weight) to about 30% (by weight) HCl.

33. A process for preparing ibuprofen which comprises carboxylating 4-isobutylstyrene with carbon monoxide in the absence of oxygen and in an anhydrous neutral or acidic medium containing tetrahydrofuran as a solvent and about 3–24 mols of an aliphatic alcohol per mol of said isobutylstyrene and no added acid at a temperature in the range of about 50°–100° C. and a carbon monoxide pressure in the range of about 400–800 psig, in the presence of (a) a mixture of palladium (II) inorganic salt and a copper (II) inorganic salt, and (b) at least one acid-stable monodentate phosphine ligand.

34. A process of claim 33 wherein the palladium (II) salt is palladium (II) chloride and the copper salt is copper (II) chloride and the ligand is triphenylphosphine.

35. A process of claim 33 wherein the palladium and the ligand are present in amounts such as to provide about 200–2000 mols of said 4-isobutylstyrene per mol of the mixture of palladium and copper salts.

36. A process of claim 1 wherein the catalyst is supported on a solvent-insoluble solid materials, 37. A process of claim 36 wherein the solid support is a carbon, 38. A process of claim 36 wherein the solid support is a zeolite, 39. A process of claim 36 wherein the solid support is a clay.

40. A process for preparing ibuprofen ester which comprises carboxylating 4-isobutylstyrene with carbon monoxide in an anhydrous neutral or acidic medium containing a compound selected from the group consisting of $HC(OR_1)_3$, $(R)_2C(OR_1)_2$, $HC(O)OR_1$, $B(OR_1)_3$, $Ti(OR)_4$ and $Al(OR_1)_3$ whiere R is hydrogen or alkyl at a temperature from about 25° to about 2002 C. and a carbon monoxide pressure from about 300 to about 3000 psig in the presence of (a) a mixture of a palladium (II) compound and a copper (II) compound and (b) at least one acid-stable ligand.

41. A process of claim 44 wherein the source of alkoxide ion is a titanium (IV) alkoxide.

42. A process of claim 44 wherein the source of alkoxide ion is a trialkyl orthoformate.

43. A process of claim 44 wherein the source of alkoxide ion is a alkyl formate.

* * * * *